United States Patent
Huovinen et al.

(10) Patent No.: US 9,453,216 B2
(45) Date of Patent: Sep. 27, 2016

(54) MUTAGENESIS METHOD

(75) Inventors: Tuomas Huovinen, Turku (FI); Urpo Lamminmäki, Vanhalinna (FI); Eeva-Christine Brockmann, Turku (FI); Markus Vehniäinen, Littonen (FI)

(73) Assignee: Turun Yliopisto (FI)

( * ) Notice: Subject to any disclaimer, the term of this patent is extended or adjusted under 35 U.S.C. 154(b) by 0 days.

(21) Appl. No.: 13/517,317

(22) PCT Filed: Dec. 21, 2010

(86) PCT No.: PCT/FI2010/051068
§ 371 (c)(1),
(2), (4) Date: Jul. 17, 2012

(87) PCT Pub. No.: WO2011/077004
PCT Pub. Date: Jun. 30, 2011

(65) Prior Publication Data
US 2013/0045507 A1 Feb. 21, 2013

(30) Foreign Application Priority Data
Dec. 21, 2009 (FI) .................. 20096371 U

(51) Int. Cl.
C12Q 1/68 (2006.01)
C12N 15/10 (2006.01)

(52) U.S. Cl.
CPC .................. *C12N 15/102* (2013.01)

(58) Field of Classification Search
None
See application file for complete search history.

(56) References Cited

U.S. PATENT DOCUMENTS 4,873,192 A * 10/1989 Kunkel .................. 435/91.1
2004/0005709 A1* 1/2004 Hoogenboom et al. ...... 435/455

FOREIGN PATENT DOCUMENTS

| WO | WO 9825871 A1 * | 6/1998 |
| WO | WO 9925871 A1 * | 5/1999 |
| WO | WO 03055975 A2 * | 7/2003 |
| WO | 2008/067035 A2 | 6/2008 |
| WO | WO 2008153935 A2 * | 12/2008 |

OTHER PUBLICATIONS

Collier et al. (Generation and identification of variants with improved purification yield of Bowman-Birk protease inhibitors carrying protein binding loops. Protein Expr. Purif. 2009-08-15 (Epub), vol. 68, No. 2, pp. 146-160).*
Fuji et al. (One-step random mutagenesis by error-prone rolling circle amplification. Nucleic Acids Res. Oct. 26, 2004, vol. 32, No. 19, e145 [online]).*
Kunkel et al. (Rapid and efficient site-specific mutagenesis without phenotypic selection, Proc. Natl. Acad. Sci. USA vol. 82, pp. 488-492, Jan. 1985).*
Vandeyar et al. (A simple and rapid method for the selection of oligodeoxynucleotide-directed mutants, Gene, 65 (1988) 129-133).*
Fujii et al. (One-step random mutagenesis by error-prone rolling circle amplification, Nucleic Acids Research, 2004, vol. 32, No. 19).*
Nelson et al. (TempliPhi, cp29 DNA Polymerase Based Rolling Circle Amplification of Templates for DNA Sequencing, BioTechniques 32:S44-S47 (Jun. 2002)).*
QuickChange Mutagenesis Kit (hereinafter "QuickChange"; Stratagene, 2003; attached).*
Collier et al. (Generation and identification of variants with improved purification yield of Bowman-Birk protease inhibitors carrying protein binding loops, Protein Expression and Purification 68 (Aug. 15, 2009) 146-160).*
Bebenek et al. (The use of native T7 DNA polymerase for site-directed mutagenesis, Nucleic Acids Research, vol. 17, No. 13, 1989).*
Su et al. (A multisite-directed mutagenesis using T7 DNA polymerase: application for reconstructing a mammalian gene, Gene, 69 (1988) 81-89).*
NEB (FAQ: What is the oligonucleotide-directed mutagenesis without phenotypic selection method?, attached, Jan. 24, 2005).*
Reagin, M.J. et al., "TempliPhi: A sequencing template preparation procedure that eliminates overnight cultures and DNA purification," J. Biomol. Tech., vol. 14, No. 2, Jun. 2003, pp. 143-148.
Li et al. "Site-Directed Mutagenesis Using Uracil-Containing Double-Stranded DNA Templates and DpnI Digestion," BioTechniques, In Forma Healthcare, US, vol. 27, No. 4, Oct. 1, 1999, pp. 734-738.
Feb. 3, 2005 (EP) Office Action—App. No. 10 838 753.1.

* cited by examiner

*Primary Examiner* — Aaron Priest
(74) *Attorney, Agent, or Firm* — Banner & Witcoff, Ltd.

(57) ABSTRACT

The present invention provides a mutagenesis method wherein a nucleic acid molecule is mutagenized with at least one mutagenesis primer in a primer extension reaction and subsequently amplified by rolling circle amplification (RCA). The method involves the step of rendering the template strand unfavorable for RCA. The method involves steps leading to selective amplification of only the mutated strand by a strand-displacing DNA polymerase. Multiple copies of the mutated plasmids are generated during multiple-primed RCA and the resulting DNA is transformed for use. The method is suitable for mutating both single-stranded and double-stranded DNA. The present invention also provides a kit for use in the mutagenesis method.

16 Claims, 6 Drawing Sheets

MUTAGENESIS METHOD

RELATED APPLICATION DATA

This application is a National Stage Application under 35 U.S.C. 371 of co-pending PCT application PCT/FI2010/051068 designating the United States and filed Dec. 21, 2010; which claims the benefit of FI patent application number 20096371 and filed Dec. 21, 2009 each of which are hereby incorporated by reference in their entireties.

FIELD OF THE INVENTION

The present invention relates to a mutagenesis method and to a kit for use in the method.

BACKGROUND OF THE INVENTION

Large randomized gene libraries are an invaluable tool for the up-to-date protein engineering. Several methods have been developed for site-directed mutagenesis sharing the common aims to gain large high quality mutant libraries with as easy and fast protocol as possible. The main factors affecting the randomized gene library quality are the unintended biases in the gene diversity, the frequency of frameshifts in the DNA sequence of the translated regions and the amount of wild type template molecules present in the final product. In the site-directed mutagenesis techniques a synthetic appropriately randomized oligonucleotide is incorporated into the target gene either by de novo gene assembly or by using wild type gene template. In the latter option, mostly used in research laboratories, the mutagenizing oligo is incorporated by primer extension in moderate temperature or PCR based methods using the wild type gene as the template.

International patent publication WO 2008/067035 discloses a technique called Unrestricted Mutagenesis and Cloning (URMAC) for mutagenizing large linear or circular nucleic acids. The technique involves a series of two PCR and three ligation steps with an addition optional enrichment PCR reaction.

One of the early primer extension methods uses uracil-containing single-stranded DNA (ss(U)DNA) template. No phenotypic selection is needed as the nascently synthesized mutant strand contains no uracil and is thus favoured in bacterial propagation resulting in reported 50% mutagenesis efficiency. This method, termed Kunkel mutagenesis, has subsequently been modified to be suitable for ds(U)DNA template by additional nitrocellulose filtering steps of alkali denatured template DNA, utilizing another oligo to destroy a unique restriction enzyme site for template sequence removal and by digesting remaining unmutated methylated ds(U)DNA template with DpnI. However, the ds(U)DNA template strategies compromise ease of template preparation with smaller library size as the primer extension with dsDNA compared to ssDNA is less efficient. Kunkel mutagenesis has even been successfully used to incorporate several mutagenesis oligos simultaneously into ss(U)DNA template. This strategy requires that the template DNA sequence is modified to contain stop codons at the sites of mutagenesis to prevent the translation of the wild type protein, as high proportion of the wild type template in the final product is the major drawback of the method.

There is a need in the art for an efficient, low-background mutagenesis method, in particular for creating large randomized gene libraries, wherein no template modifications are needed and which yields in ample supplies of transformable DNA circumventing the well-known problem that transformation of the DNA to host cells is the biggest bottleneck in the gene library production line.

BRIEF DESCRIPTION OF THE INVENTION

An object of the present invention is to provide novel means and methods for mutagenizing nucleic acid molecules. In particular, an object of the present invention is to provide means and methods for efficient mutagenesis of both single-stranded and double-stranded DNA with low template background and increase in the yield of mutated DNA.

The present invention provides a method of mutagenizing a nucleic acid molecule. The method comprises the steps of a) providing a template comprising a target nucleic acid molecule in a circular DNA vector, b) providing at least one mutagenesis primer containing the mutations to be introduced into the target nucleic acid molecule, c) annealing the mutagenesis primer to the target nucleic acid molecule, d) carrying out a primer extension and ligation reaction to form a double-stranded heteroduplex wherein one strand is a template strand and the other strand is a newly synthesized mutated strand, e) rendering the template strand unfavourable for rolling circle amplification (RCA), f) amplifying the mutated strand by multiple-primed rolling circle amplification, and g) transforming the amplified and recircularized DNA to a suitable host.

In some embodiments, the method comprises a further step between steps f) and g), wherein the amplified DNA is (i) digested, (ii) digested and ligated, or (iii) reduced to plasmid-size units using recombination.

In some embodiments, the template of step a) contains uracil and the template strand is rendered unfavourable for the RCA by a treatment with uracil-DNA glycosylase (UDG) in step e). In further embodiments, the template may be obtained from an ung−/dut− *E. coli* strain.

In other embodiments, the template of step a) is methylated uridylated dsDNA which is rendered unfavourable for the RCA by a treatment with DpnI restriction enzyme and UDG in step e). In further embodiments, the template may be obtained from a dam+/ung−/dut− *E. coli* strain.

In further embodiments, the template of step a) contains methyl groups and the template strand is rendered unfavourable for the RCA in step e) by a treatment with a restriction enzyme capable of digesting methylated DNA but not unmethylated DNA. In such embodiments, the restriction enzyme is DpnI and/or the template may be obtained from a dam+ *E. coli* strain.

In further embodiments, the primer extension reaction of step c) is carried out in the presence of a methylating agent and the template strand is rendered unfavourable for the RCA by a treatment with a restriction enzyme capable of nicking the unmethylated strand leaving the methylated strand intact such, as MspI and HaeIII. In such embodiments, the template may be obtained from a dam− *E. coli* strain.

In still further embodiments, the template strand is rendered unfavourable for the RCA in step e) by a treatment with a nicking endonuclease having a recognition site only in the template strand. Such embodiments may further comprise a treatment with an exonuclease after the endonuclease treatment.

The present invention also provides a kit for use in the method according to the present invention and all its embodiments. The kit comprises a) a first enzyme mixture comprising reagents for primer extension and ligation including a DNA polymerase without significant strand displacement activity, dNTP's, a DNA ligase, ATP and DTT in appropriate buffers; b) a selective template inactivating enzyme; and c) a second enzyme mixture comprising reagents for RCA, including a strand-displacing DNA polymerase such as phi29 DNA polymerase, random primers and dNTP's in appropriate buffers.

In some embodiments, the kit comprises UDG as said selective template inactivating enzyme and further comprises an ung−/dut− E. coli strain. In other embodiments, the kit comprises DpnI as said selective template inactivating enzyme. In further embodiments, said selective template inactivating enzyme is a restriction enzyme capable of nicking the unmethylated strand and leaving the methylated strand intact, such as MspI or HaeIII, and the kit further comprises a strain deficient in dam-methylation, such as a dam− E. coli strain. In other embodiments, said selective template inactivating enzyme is a restriction enzyme capable of nicking a methylated strand while leaving an unmethylated strand intact, and the kit further comprises a strain capable of dam-methylation, such as a dam+ E. coli strain. In still further embodiments, said selective template inactivating enzyme is a nicking endonuclease.

Optionally, the kit may further comprise at least one component selected from a group consisting of a T4 DNA ligase for recircularization of DNA, a DNA purification column for the ligated DNA and competent cells for transformation.

Further specific embodiments of the present method and kit are set forth in the dependent claims.

Other objects, embodiments, aspects, details and advantages of the present invention will become apparent from the following drawings, detailed description and examples.

BRIEF DESCRIPTION OF THE DRAWINGS

In the following the invention will be described in greater detail by means of preferred embodiments with reference to the attached drawings, in which.

DETAILED DESCRIPTION OF THE INVENTION

Figure 1:
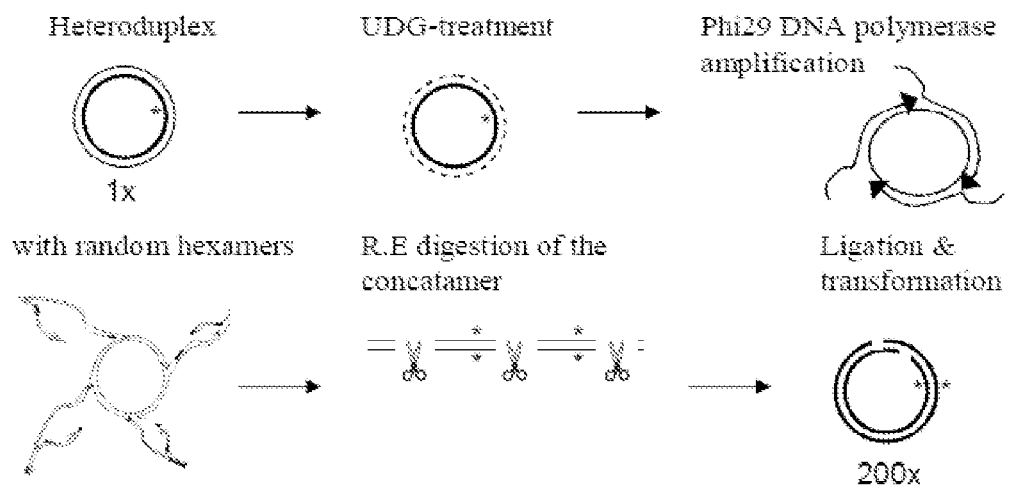
FIG. 1 is a schematic representation of the present mutagenesis method wherein a DNA heteroduplex generated in a traditional Kunkel mutagenesis reaction is treated with uracil-DNA glycosylase (UDG), amplified by rolling circle amplification, and subsequently digested and self-ligated to form multiple copies of the mutated DNA.

The present invention is based on studies for developing an efficient mutagenesis method with low template background and increase in the yield of mutated DNA.

In one aspect, the present invention provides a method wherein a nucleic acid molecule is mutagenized with a mutagenesis primer in a primer extension reaction and subsequently amplified by rolling circle amplification (RCA) in some occasions also known as multiply-primed displacement amplification (MDA) or Multiply-primed rolling circle amplification (MPRCA) favouring the amplification of the newly synthesized, mutagenized nucleic acid molecule. Several alternatives are provided as how to achieve the selective amplification.

The method may be used for site-directed mutagenesis wherein targeted mutations are introduced into one or more desired positions of the template polynucleotide. This may be achieved by classic primer extension mutagenesis using a mutagenesis primer containing one or more desired mutations relative to the template polynucleotide. The mutagenesis primer may be a synthetic oligonucleotide or a PCR product, and it may include one or more desired substitutions, deletions, additions or any desired combination thereof. Means and methods for producing such primers are readily available in the art. The oligonucleotide or PCR product used as primer must be 5'-phosphorylated for ligation. This can be achieved by enzymatic phosphorylation reaction, by enzymatic digestion of the 5' end of the DNA or by conjugation in a chemical reaction.

Alternatively, the method may be used for random mutagenesis. In such cases, mutations may be introduced into the mutagenesis primer during its synthesis e.g. by means of error-prone PCR. Randomly mutagenized oligonucleotides may also be used as mutagenesis primers. Means and methods for obtaining such random mutagenesis primers are known in the art.

PCR products have some advantages over oligonucleotides as mutagenesis primers. Long DNA fragments containing many mutations can be incorporated into the template gene in one reaction. For example, a gene segment of interest can be randomly mutated by PCR and joined to the template gene by the method of the present invention. Also a gene library containing several site-directed mutations at several locations can be amplified by PCR and combined to the target polynucleotide. To enhance PCR product incorporation, asymmetric PCR product may be produced complementary to the template DNA if single stranded DNA is used as template. As an alternative to a PCR product, dsDNA cut from another gene library may be used as a mutagenesis primer and joined to the target DNA by the present method provided that there is enough complementarity in the annealing 5"- and 3'-end nucleotides of the template and the digested fragment.

A further alternative for providing randomly mutagenized nucleic acids is to use error-prone RCA. This may be achieved by reducing the fidelity of a DNA polymerase by performing the RCA in the presence of $MnCl_2$ or decreasing the amount of input DNA.

Herein the term "target gene" or "target polynucleotide" refers to one or more genes, or fragments thereof, to be mutated by the present method. The target gene may encode any desired one or more proteins including, but not limited to, an antibody or a binding fragment of an antibody, such as a Fab, $F(ab')_2$, or Fab' fragment. In some embodiments, the region to be mutated is a variable region, preferably a hypervariable region, of an antibody. In particular, the region to be mutated may be one or more of the complementarity-determining regions (i.e. CDRs) of an antibody. In addition to coding regions, noncoding regions may be mutated by the method such as but not restricted to gene regulatory DNA regions and aptamers.

Prior to mutagenesis, the target gene is cloned to a DNA vector by standard methods known in the art. Herein, such a cloned target gene is referred to as "a template gene". Likewise, the term "template DNA" refers to the vector, such as a plasmid or phagemid, containing the target gene. Herein, the terms "template" and "parental template" may be used interchangeably.

The term "heteroduplex" as used herein refers to a double-stranded nucleic acid molecule wherein one strand (the template strand) is non-mutated and the other, in vitro synthesized strand contains the desired mutations (mutated heteroduplex strand).

When the present method is used to mutate single-stranded DNA (ssDNA), the target gene is cloned to a phagemid. Herein the term "phagemid" refers to a plasmid-based cloning vector carrying a portion of a phage genome. Upon co-infection of a host with a helper phage, the phagemid is packaged as ssDNA into phage (e.g. M13) particles. When the present invention is used to mutate double-stranded DNA (dsDNA), the target gene may be cloned to any desired plasmid containing at least one unique restriction enzyme cut-site. Herein the term "plasmid" refers to an independently replicating extra-chromosomal DNA. Typically, plasmids are double-stranded and circular.

In some embodiments, ssDNA template may be produced from dsDNA using nicking endonucleases as know to a person skilled in the art.

When dsDNA is used as a template, the double-stranded structure must be opened prior to mutagenesis. This may be achieved by standard methods known in the art including, but not limited to alkaline or heat denaturation.

There are different ways of rendering parental template strand disfavourable for rolling circle amplification. One alternative is to use uracil-containing template DNA. This may be achieved e.g. by replicating the template DNA in the presence of uridine in an ung–/dut– E. coli strain, such as BW313 and CJ236, which are deficient in the enzyme dUTP pyrophosphatase (dut–) resulting in an increased incorporation of uracil in place of thymine in the DNA. The incorporated uracil is not removed from the DNA in these strains due to an inactivating point mutation in uracil-DNA glycosylase (ung–). When phagemids are used as cloning vectors, the template DNA may subsequently be extracted as ss(U) DNA from filamentous phage, such as M13, particles produced in ung–/dut– E. coli cell strains. When double-stranded plasmids are used as cloning vectors, the template DNA may be extracted as ds(U)DNA using any suitable method known in the art.

E. coli strain with the genotype dut– is deficient in the enzyme dUTPase resulting in an increased intracellular pool of dUTP. E. coli strain with the genotype ung– is deficient in the uracil glycosylase activity abolishing the ability to remove incorporated uracil. Thus, an E. coli strain with ung–/dut– genotype is defined as a strain with deficiencies in both enzyme activities resulting in increased stable incorporation of uracil into DNA. E. coli strain with the genotype dam– is deficient in the Dam methylase activity resulting in unmethylated DNA at sites with 5"-GATC-3" sequence. Correspondingly, dam+ E. coli strains are active in Dam methylation resulting in methylation of the adenine in the 5"-GATC-3" sequence. Therefore, a strain dam+/ung–/dut– is defined as a strain that methylates DNA at 5"-GATC-3" sequences and has uracil in the DNA.

Uridylated template DNA in the form of ss(U)DNA or ds(U)DNA may also be prepared enzymatically using for example T7 DNA polymerase together with dNTP's and dUTP.

When ds(U)DNA is used as a template, the double-stranded structure must be opened prior to mutagenesis. This may be achieved by standard methods known in the art including, but not limited to alkaline or heat denaturation.

In this embodiment of the present method, the mutagenesis primer is used to prime the complementary strand synthesis of the uridylated template DNA. Annealing of the mutagenesis primer to the uridylated template DNA requires that the mutagenesis primer has enough complementarity in its 5' and 3' ends with the template molecule. Typically, there are about 15 to about 30 complementary nucleotides in the 5' end and about 15 to about 30 complementary nucleotides in the 3' end of the primer relative to the target DNA. However, shorter complementary segments may also be used, especially when one or few consecutive nucleotides are targeted for mutagenesis. Primer extension in the presence of a DNA polymerase, such as T7 or T4 polymerase, and ligation with a DNA ligase, such as T4 ligase, results in a ligated heteroduplex, i.e. covalently closed circular DNA (cccDNA), in which one stand (the template strand) contains uracil and is non-mutated and the other, in vitro synthesized strand contains the desired mutations but no uracil.

In classic Kunkel mutagenesis, the resultant heteroduplex is then transformed to an ung+/dut+ E. coli strain that does not support the presence of uracil. Because the uracil-containing DNA is biologically inactivated in such a host, the mutated non-uridylated strand should have a strong selective advantage over the uridylated template when the heteroduplex DNA is propagated in the E. coli cells. However, in connection with the present invention it was demonstrated that 80% of the clones considered as mutated still contained non-mutated template DNA. In contrast, only 0-5% of the clones mutated by the present method contained non-mutated template DNA (Example 1, Table 1).

In this embodiment of the present method, instead of direct transformation the ligated heteroduplex is treated with uracil-N-glycosylase (UDG) to hydrolyze uracils in the heteroduplex. This renders the uracil-containing heteroduplex strand incapable of being copied by DNA polymerases. UDG creates abasic sites which have been reported to cause stalling of DNA polymerases. Homologs of UDG are available in the art and may equally be used in the present method.

Another way of rendering parental uridylated dsDNA template unfavourable for rolling circle amplification is to enhance the background removal with a methylated DNA digesting enzyme, such as DpnI, in addition to UDG. This method is applicable if the dsDNA template is extracted from dam+/ung−/dut− E. coli strain or the uridylated DNA is methylated with Dam methylase which transfers a methyl group from S-adenosylmethionine to the adenine of the sequence 5"-GATC-3".

Introduction of one or more mutations into the target gene may be performed by a primer extension reaction and subsequent ligation as described in more detail for uridylated templates. Next, parental template DNA is removed by digestion with a restriction enzyme, such as DpnI, which digests methylated DNA but not in vitro newly synthesized unmethylated DNA. DpnI is commercially available, and suitable digestion conditions are readily appreciated by a person skilled in the art. In some embodiments, DpnI digestion may be used in combination with the UDG to further increase the efficiency.

Still another way of rendering parental template DNA unfavourable for rolling circle amplification is to use DNA extracted from dam+ E. coli strain as a template. Such a template is methylated and may be extracted either as ssDNA or dsDNA depending on the cloning vector used. After primer extension and ligation the parental template DNA is removed by digestion with a restriction enzyme, which digests methylated DNA but not in vitro newly synthesized unmethylated DNA, such as DpnI.

Still another way of rendering parental template DNA unfavourable the rolling circle amplification is to use template DNA isolated from a dam− E. coli strain which are available in the art, such as JM110, SCS110, ER2925, or GM2929 strain. Again, template DNA may be extracted as ssDNA or dsDNA depending on the cloning vector used by suitable methods known in the art.

In this alternative, primer extension reaction is carried out in the presence of a methylating agent, such as 5-methyl-dCTP, in order to add methyl groups into the newly synthesized mutagenized DNA. Subsequently, the unmethylated parental template DNA is removed with a restriction enzyme, such as MspI or HaeIII, capable of digesting the unmethylated strand and leaving the methylated strand intact. To enhance the effect, exonucleases, including 5'-exonucleases such as Lambda Exonuclease, T7 Exonuclease, and 3'-exonucleases such as Exonuclease III may be used to remove parental strand from nicks created with MspI or HaeIII. Suitable restriction enzymes and exonucleases are commercially available, and suitable digestion conditions are readily appreciated by a person skilled in the art.

Parental template DNA may be rendered unfavourable for rolling circle amplification also by appropriate sequence specific nicking endonucleases that cleave only one of the strands. For this approach, nicking endonucleases having recognition sites in such orientation that the template strand is nicked is used. The nicked template strand is disfavoured in the rolling circle amplification as compared to the mutated strand. The amplification of the nicked template strand may be further inhibited by 3'-exonuclease, such as exonuclease III, treatment. There are several nicking endonucleases commercially available that are suitable for this approach. Examples of such enzymes include, but are not limited to Nb.BbvCI, Nb.BsmI, Nb.BsrDI, Nb.BtsI, Nt.AlwI, Nt.BbvCI, Nt.BsmAI, Nt.BspQI, Nt.BstNBI, and Nt.CviPII.

In the next step of the present method, the mutated heteroduplex strand is selectively amplified with a highly processive strand-displacing polymerase in a rolling circle amplification reaction. Suitable DNA polymerases include, but are not limited to, phi29 DNA polymerase, Bst DNA polymerase, and Bsu DNA polymerase. Phi29 DNA polymerase is a preferred polymerase. Multiply-primed rolling circle amplification (MPRCA) may used to enhance the efficiency of the amplification. This is achieved by using multiple random DNA primers, exoresistant random DNA primers, or random RNA primers in the amplification reaction. Preferably, the primers are hexamers or heptamers. Multiple specific primers may also be used. Due to the UDG treatment and multiple priming, the DNA polymerase amplifies the intact mutated strand selectively producing multiple copies of the vector. The concatemer thus formed is then digested with a restriction enzyme having only one cut-site per vector and self-ligated with T4 DNA ligase to recirculize the products. Suitable restriction enzymes depend on the vector used and include, but are not limited to AatII, AdeI, ApaI, BamHI, BglII, EcoRI, HindIII, KpnI, NdeI, NotI, PaeI, PstI, SacI, XbaI, and XhoI. The vectors are then transformed to a suitable host, such as E. coli or yeast.

In some embodiments, recombination such as the Cre-Lox technology may be used instead of digestion and ligation of the DNA concatemer. To this end, LoxP1 sequence is inserted to the vector to be amplified by RCA. Addition of cre recombinase starts the circularization and reduction of the linear DNA concatemer to monomer units. LoxP makes recircularization faster and easier compared to digestion and ligation, but the requirement for loxP sequence in the template vector limits the universal applicability of the method.

Generally, phi29 DNA polymerase is a high fidelity enzyme with low mutation rate. However, the mutation rate in MPRCA can be increased by using random DNA primers, such as random hexamers, in excess high concentrations as compared to the amount of DNA to be amplified. Thus, this embodiment of the present method provides a further tool for random mutagenesis.

The background level of wild type, i.e. non-mutated, template DNA in the transformants obtained by the present method is extremely low. As demonstrated in the Examples, even 90% or 100% genetic mutagenesis efficiency may be achieved. Other preferred genetic mutagenesis efficiencies include 95%, 96%, 97%, 98% and 99%.

By the present method, it is possible to achieve a significant increase in the functional mutagenesis efficiency as compared to that of the traditional Kunkel method. In the case of ss(U)DNA, functional mutagenesis efficiencies close to the maximum theoretical efficiency of 78% were achieved. Over 10-fold increase in the functional mutagenesis efficiency of ds(U) was achieved by the present method as compared to the corresponding efficiency of the Kunkel method.

Furthermore, the yield of mutated clones obtainable by the present method is extremely high. For example, 10 ng template DNA yielded $3.6\pm1.3\times10^5$ cfu by classic Kunkel reaction containing $2.2\pm1.3\times10^5$ mutated clones as determined by genetic analysis. The same amount of template DNA yielded $8.1\pm1.7\times10^7$ cfu by the present method, of which all clones were mutated based on the genetic analysis, which is over 300-fold more mutated clones than gained with the classic Kunkel reaction (see Table 1).

The present method may be used to create a library of molecules, such as antibodies. In such embodiments, multiple mutagenesis primers may be used simultaneously to mutate the target nucleic acid. Alternatively or in addition, multiple target nucleic acid molecules may be mutagenized simultaneously in a single mutagenesis reaction. Thus, the library created may contain extensive diversity.

The gene libraries obtainable by the present method may be larger than those created by traditional PCR-based methods. Furthermore, large gene libraries may be created with higher mutagenesis efficiency than can be achieved with known methods. In the present method, there is no need for commonly used special selection features (STOP-codons, restriction sites etc.) in the mutagenized gene template for reducing the template contamination in the mutagenesis product. The present mutagenesis method does not include a bimolecular cloning step (insert+vector) where the insert DNA and the cloning vector are cut with compatible restriction enzymes followed by a ligation. Owing to this, the present mutagenesis method enables straightforward introduction of (random) mutations in a DNA segment, the location and the length of which can be freely selected. For example, random mutagenesis can be targeted into a specific domain within a multi-domain enzyme.

Other advantages of the present method include that it is time efficient and not labour intensive since any bimolecular cloning steps are not required. Furthermore, the present method does not need template DNA in large quantities, which is normally the case for mutagenesis methods used for creating large libraries of antibodies.

The present invention further provides a kit for use in the method according to the present invention. The kit comprises a first and a second enzyme mixture, and a selective enzyme inactivating the template. The first mixture comprises reagents for primer extension and ligation including a DNA polymerase without significant strand displacement activity (e.g. T7 or T4 DNA polymerase), dNTP's, a DNA ligase (e.g. T4 ligase), ATP and DTT in appropriate reaction/ storage buffers. The second mixture comprises reagents for RCA, including a strand-displacing DNA polymerase (e.g. phi29 DNA polymerase), random primers and dNTP's in appropriate reaction/storage buffers. Optionally, the kit may further comprise additional DNA ligase (e.g. T4 ligase) for recircularization of fragment DNA, a DNA purification column for the ligated DNA and/or competent cells for transformation.

In embodiments wherein the template DNA is uridylated, UDG is provided as a selective template inactivating enzyme, and the kit further comprises an ung–/dut– E. coli strain.

In embodiments wherein methylated template is used, the kit comprises the same components except that instead of UDG, the selective template inactivating enzyme is DpnI or another enzyme capable of digesting methylated DNA but not unmethylated DNA. Also, no need exists to provide a strain as methylated DNA may be produced in most of the commonly used E. coli strains.

In embodiments wherein unmethylated template is used, the kit comprises the same components except that the selective template inactivating enzyme is a restriction enzyme capable of nicking the unmethylated strand of the heteroduplex, such as MspI or HaeIII, and a strain deficient in dam-methylation such as JM110, SCS110, ER2925 or GM2929 is provided in the kit.

In embodiments wherein nicking endonuclease is used, the kit comprises the same components except that the selective template inactivating enzyme is a nicking endonuclease. Also, no need exists to provide a strain as any DNA produced with commonly used E. coli strains is suitable as a template.

It will be obvious to a person skilled in the art that, as the technology advances, the inventive concept can be implemented in various ways. The invention and its embodiments are not limited to the examples described above but may vary within the scope of the claims.

Example 1

Mutagenesis of CDR-H3 Loop Region in Single-Chain Fv Anti-Body Gene

Target for the mutagenesis was a CDR-H3 loop region of single-chain Fv antibody gene fused to TEM-1 β-lactamase gene on a phagemid vector termed pAKBLA3-scFv.

The template DNA was subjected to different treatments in order to assess the efficacy of the present mutagenesis method.

Primer Extension Mutagenesis

The template sequence contained three stop codons at the site of mutagenesis. The mutagenesis oligonucleotide was designed to restore the open reading frame. The oligonucleotide mix EB120 used in this experiment contained 28 hybridizing base pairs (bp) in the 5' end, 25 hybridizing bp in the 3' end and seven random NNN codons between them (5'-CTAGTGTACCCTGACCCCAGTCCATAGC NNNNNNNNNNNNNNNNNNNNN ACGAGCACAG-TAGTAGACAGCCGTG-3'; SEQ ID NO:1). In theory, 78% of the mutated clones should have the open reading frame and thus result in an ampicillin resistant clone.

The mutagenesis oligo EB120 was purchased from (TAG Copenhagen, Copenhagen, Denmark). The oligo was phosphorylated in 20 µl reaction containing 5 µM oligo EB120, 1 mM ATP, 5 mM DTT, 70 mM Tris-HCl (pH 7.6), 10 mM MgCl$_2$ and 20 U T4 polynucleotide kinase (New England Biolabs) for 1 h at 37° C. Phage stock of the pAKBLA3-scFv phagemid was prepared from E. coli CJ236 strain with standard methods with the exception that the CJ236 growth medium was supplemented with 6 μg/ml uridine. The ss(U) DNA was extracted with Qiaspin M13 Kit (Qiagen) according to manufacturer's instructions. 5 pmol phosphorylated primer was annealed to 1 μg single stranded pAKBLA3-scFv phagemid in 1× T4 DNA ligase buffer (New England Biolabs). The annealing was done in PCR machine with the following program: 90° C. for 2 min, 70° C. for 2 min, 50° C. for 5 min, 20° C. for 5 min, 4° C. for 5 min and finally set on ice for 10 min.

The following components were added to the 15 μl annealing reaction while keeping on ice: 1 μl 25 mM $MgCl_2$, 2.5 μl 10 mM ATP, 2 μl 100 mM DTT, 1 μl 25 mM dNTP, 3.5 U T7 DNA polymerase (New England Biolabs) and 3 Weiss Units T4 DNA ligase (New England Biolabs). The reaction was incubated at room temperature for 3 h.

The obtained heteroduplex was either directly transformed to *E. coli* XL-1 Blue host (the sample denoted as −UDG) or subjected to a UDG treatment (the sample denoted as +UDG).

Removal of Uracil by UDG Treatment

1 μg Kunkel heteroduplex was treated with UDG in a 25 μl reaction in 1×UDG reaction buffer (New England Biolabs) containing 20 mM Tris-HCl (pH 8.0), 1 mM EDTA, 1 mM DTT and 10 U UDG (New England Biolabs) for 1 h at 37° C. A control sample without UDG treatment was incubated in the same conditions as the UDG treated sample with the exception that the UDG was replaced with $H_2O$. Reactions were purified with Qiagen PCR purification Kit (Qiagen) and eluted into 50 μl of 10 mM Tris-HCl (pH 8.5). DNA concentrations were determined with Nanodrop (Nanodrop Technologies, Wilmington, USA).

Rolling Circle Amplification 10 ng DNA samples of the UDG treated (the sample denoted as +UDG +RCA) and nontreated (the sample denoted as −UDG +RCA) reactions were amplified in a 20 μl reaction with 10 mM dNTP's (Finnzymes), 50 μM exoresistant or normal random hexamers (Fermentas), 1× phi29 DNA polymerase buffer (Fermentas) containing 50 mM Tris-HCl (pH 7.5), 10 mM $MgCl_2$, 10 mM $(NH_4)SO_4$, 4 mM DTT; 0.05 U Yeast Pyrophosphatase (Fermentas) and 10 U Phi29 DNA polymerase. The reactions were incubated overnight at 30° C. and inactivated for 10 min at 70° C.

Digestion and Recircularization of the DNA Concatemer

The amplified DNA samples were digested for 2 h at 37° C. with 20 U HindIII (Fermentas) in a 50 μl reaction supplemented with 1× reaction buffer (Fermentas) containing 10 mM Tris-HCl (pH 8.5), 10 mM $MgCl_2$, 100 mM KCl and 0.1 mg/ml BSA. The reactions were purified with Qiagen PCR purification kit and eluted into 50 μl 10 mM Tris-HCl (pH 8.5). DNA concentrations were determined with Nanodrop (Thermo Scientific).

1 μg samples of the purified HindIII digested DNA were recircularized in 200 μl reaction volume with 1× T4 DNA Ligase buffer (Fermentas) containing 40 mM Tris-HCl (pH 7.8), 10 mM $MgCl_2$, 10 mM DTT and 0.5 mM ATP. Reaction was supplemented with 25 U T4 DNA Ligase (Fermentas) and incubated overnight at 16° C. Ligations were purified with Qiagen PCR purification Kit (Qiagen), eluted in 50 μl Tris-HCl (pH 8.5) and DNA concentrations were determined with Nanodrop (Thermo Scientific).

Transformation and Plating 10 ng DNA samples (−UDG, +UDG −RCA, +UDG +RCA) were electroporated into XL1 Blue electrocompetent cells (Stratagene) with GenePulser (BioRad), recovered in 1 ml SOC (LB: 10 g tryptone, 5 g yeast extract, 10 g NaCl per 1 l, pH 7.0, with 10 mM $MgCl_2$ and 0.4% W/V glucose) for 1 h. Dilutions were made and 100 μl was spread on LA (Luria-Bertani broth agar) plates containing 25 μg/ml chloramphenicol and 100 μM IPTG (Isopropyl β-D-1-thiogalactopyranoside), and to other LA plates containing 100 μg/ml ampicillin in addition to chloramphenicol and IPTG. Plates were incubated overnight at 37° C. and the colonies counted. In the case of DNA library pool analysis 4 ml SB (Super broth: 30 g tryptone, 20 g yeast extract, 10 g MOPS per 1 l pH 7.0) was added on the 1 ml SOC after the recovery time and supplemented with 25 μg/ml chloramphenicol. Cultures were grown overnight at 37° C. 300 rpm and the DNA was extracted with Qiagen miniprep kit (Qiagen) according to manufacturer's instructions.

Functional Analysis

Figure 2:
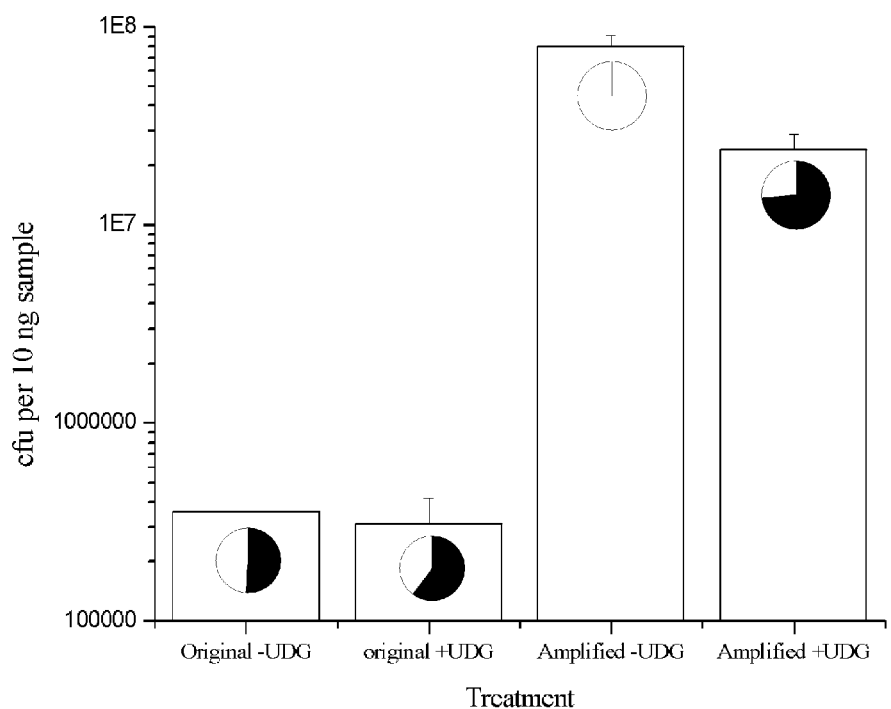
FIG. 2 illustrates the effect of UDG treatment on ss(U) DNA mutagenesis reactions with selective rolling circle amplification primed with exoresistant hexamers. The pie chart illustrates the proportion of functionally mutated clones (black) versus non-functionally mutated and non-mutated clones (white).

The mutagenesis efficiency, ratio of ampicillin resistant to chloramphenicol/ampicillin resistant clones, gained from direct transformation of the classic Kunkel heteroduplex (−UDG) was 51.3±7.6% based on functional mutagenesis assay (Table 1). After UDG treatment the mutagenesis efficiency was slightly improved (+UDG −RCA) and after selective RCA (+UDG+RCA) functional mutagenesis efficiencies of 65.1±4.7% and 73.6±11.2% were achieved depending on whether exoresistant or nonmodified random hexamers were used in the amplification reaction. Interestingly, if the heteroduplex was amplified with RCA prior to UDG treatment and transformed, the resulting mutagenesis efficiency was decreased to 0.1±0.01%. Thus, the selectivity for mutated sequences is dependent on UDG treatment (FIG. 2).

TABLE 1

The effect of selective RCA on primer extension mutagenesis with ss(U)DNA template

| | Treatment | | | | |
|---|---|---|---|---|---|
| | A. Extended & ligated −UDG | B. Extended & ligated +UDG | C. RCA of A −UDG | D. RCA of B +UDG | E. RCA of B +UDG |
| Random hexamers | none | none | exoresistant | exoresistant | Normal |
| Functional mutagenesis efficiency (%)[a] | 51.3 ± 7.6 | 60.4 ± 18.0 | 0.1 ± 0.01 | 65.1 ± 4.7 | 73.6 ± 11.2 |
| Genetical mutagenesis efficiency (%)[b] | 60 | 65 | N.D. | 90 | 100 |
| Template DNA present in mutated clones (%)[c] | 80 | 80 | N.D. | 5 | 0 |
| Transformants per 10 ng DNA sample (cfu) | 3.6 ± 1.3 × $10^5$ | 3.1 ± 1.1 × $10^5$ | 8.0 ± 1.1 × $10^7$ | 2.4 ± 0.5 × $10^7$ | 8.1 ± 1.7 × $10^7$ |

[a]Maximum theoretical functional mutagenesis efficiency is 78%.
[b]Determined by restriction mapping PCR products of 20 cm-resistent clones
[c]Based on colony PCR of 20 cm/amp-resistant clones In addition to increasing the amount of mutated clones in the population, there was an increase in the total number of transformants gained from the transformation (FIG. 2). Transforming 10 ng heteroduplex directly yielded $3.6\pm1.3\times10^5$ cfu's, but by amplifying the 10 ng sample by selective RCA and transforming all amplified and ligated DNA, mutagenesis libraries of $8.1\pm1.7\times10^7$ cfu's were gained.

Genetic Analysis

The transformants were screened with colony PCR to verify the mutagenesis efficiencies. The incorporated mutations destroy SacII restriction enzyme site located in the template CDR H3 loop region and thus, an amplified 940 bp PCR product is resistant to cleavage with SacII if mutagenesis has been successful. There were 8/20 cleaved amplicons, 8/20 cleavage-resistant amplicons and 4/20 partially digested amplicons among the classic Kunkel heteroduplex transformants picked from the chloramphenicol plates for analysis. The four samples were classified as partially digested, because the wild type template control amplicon was totally digested with SacII in the same conditions. Partial digestion indicated that both mutated and nonmutated phagemids had propagated in those clones.

In contrast, 20/20 analysed transformants originating from the UDG treated and selectively amplified library primed with unmodified random hexamers were resistant to SacII digestion indicating 100% mutagenesis efficiency. The sizes of the PCR products were uniform indicating that the selective RCA has not caused DNA rearrangements. In addition, no double template problem was noticed with the selectively amplified transformants. In the case of exoresistant hexamers, 2/20 clones were non-mutated and 18/20 mutated.

Finding out that double template was present in 4/20 transformants of the classic Kunkel mutagenesis reaction on chloramphenicol plates, we decided to test colonies also from the cm/amp-plates for the presence of template DNA. In this screen there is no possibility for overlapping cm- and amp-resistant colonies misleading conclusions. Instead of digesting the amplicon, a primer pair was used in which the forward primer hybridized only to the unmutated template DNA and the reverse primer outside the mutated region. By this way also smaller amounts of template DNA could be detected. In the case of unamplified heteroduplex 16/20 clones yielded PCR product indicating that the unmutated template DNA was still present in 80% of the clones considered to be mutated. Of the selectively amplified transformants 1/20 PCR products were observed if exoresistant primers were used in the amplification and 0/20 PCR products if normal hexamer primers were applied.

Figure 3:
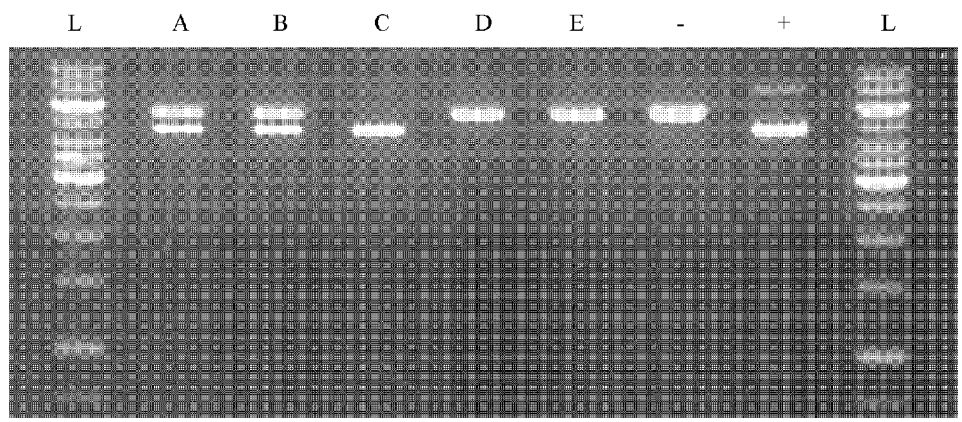
FIG. 3 illustrates the success of mutagenesis after different treatments by digestion of phagemid DNA samples with HindIII and SacII. Successful mutation destroys the SacII restriction site resulting in a linear 5.4 kb DNA fragment, whereas non-mutated DNA is digested in two, 4.5 kb and 0.9 kb, DNA fragments. (A) heteroduplex −UDG, (B) heteroduplex +UDG, (C) heteroduplex −UDG +RCA, (D) heteroduplex +UDG +RCA with exoresistant random primers, (E) heteroduplex +UDG +RCA with normal random primers. (L) 1 kb Fermentas DNA Ladder.

The single clone screening results were confirmed by digesting miniprep DNA extracted from overnight grown cells transformed with the sample libraries (FIG. 3). HindIII site is outside the target gene and hence present in all phagemids whereas SacII site, present in the wild type gene, is destroyed during successful mutagenesis. The nonmutated phagemids are cleaved to 4506 bp and 868 bp size fragments and the mutated phagemids are linear 5374 bp fragments. Unfortunately, the less intensively staining 868 bp fragment is hardly visible in the figure, but the bigger 4.5 kb and 5.4 kb fragments are clearly visible. As the FIG. 3 shows there are both mutated and nonmutated phagemids present in the samples transformed with the Kunkel heteroduplex with and without UDG treatment (A, B). The amplified phagemid pool without UDG treatment has no visible amount of mutated phagemids (C) where as in the UDG treated and amplified samples only mutated phagemids are visible.

Example 2

Mutagenesis of CDR-H1 Loop Region in scFv Antibody Gene

The present mutagenesis method was further tested by mutagenizing the CDR H1 loop of the scFv antibody gene using ss(U)DNA as template.

Primer EB104 has 23 hybridizing bases in the 5' end, 19 hybridizing bases in the 3' end and two randomized codon positions X12 and X13 in the middle separated by a TAO codon (5'-CA GCC TCC GGA TTT ACG TTC TCC X12 TAO X13 ATG CAC TGG GTC CGT CAG G-3'; SEQ ID NO:2). The primer was synthesized by inserting DNA trinucleotides to the oligo for tailored codon diversity.

The results were similar to the more detailed Example 1 described above with an increase in the mutagenesis efficiency from 15% to 100% by selective amplification analysed by restriction digestion of 20 phagemid clones.

Minipreps of 8 mutated clones originating from the Kunkel heteroduplex transformation and 10 mutated clones from the selectively amplified DNA transformation were prepared and sequenced (Table 2). 6/8 transformed Kunkel heteroduplex clones were mutated correctly of which two clones had the same sequence. Likewise, 7/10 clones of the selective RCA sample were correctly mutated of which two clones had the same sequence. Two clones in both samples contained trinucleotide deletions in the randomized positions probably due to incomplete primer synthesis and one clone of the selective RCA subset yielded unreadable sequence. As conclusion, both the original sample and the selectively amplified sample yield equal distribution in sequence variability based on this set of sequences.

TABLE 2

Sequence details of the correctly mutated clones of the CDR H1 mutagenesis study
Designed diversity in codon position X12: 16.7% of TCT, AAC, GAC, CGT, ACT and GGT.
Designed diversity in codon position X13: 20% of TAC, GGT, GCT, TGG and TCT.

|  | X12 | X13 |
|---|---|---|
| Template Kunkel heteroduplex | | |
| Clone1 | ACT | TAC |
| Clone2 | GGT | TGG |
| Clone3 | AAC | GGT |
| Clone4 | TCT | GCT |
| Clone5 | TCT | TGG |
| Clone6 | TCT | GCT |
| Selective RCA | | |
| Clone1 | AAC | TAC |
| Clone2 | GAC | TAC |
| Clone3 | ACT | TGG |
| Clone4 | GAC | GCT |

TABLE 2-continued

Sequence details of the correctly mutated
clones of the CDR H1 mutagenesis study
Designed diversity in codon position X12:
16.7% of TCT, AAC, GAC, CGT, ACT and GGT.
Designed diversity in codon position X13:
20% of TAC, GGT, GCT, TGG and TCT.

|  | X12 | X13 |
| --- | --- | --- |
| Clone5 | GAC | TAC |
| Clone6 | GAC | TCT |
| Clone7 | CGT | TCT |

Example 3

Recircularization of DNA Concatemer by Cre-Lox Technology

Figure 4:
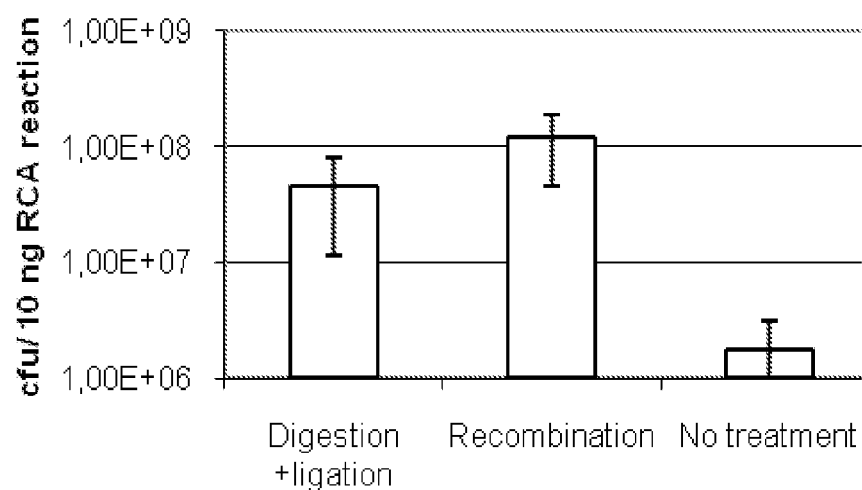
FIG. 4 shows the number of transformants obtained from 10 ng of an RCA amplified DNA sample by using recombination, digestion/ligation or no treatment.
Figure 5:
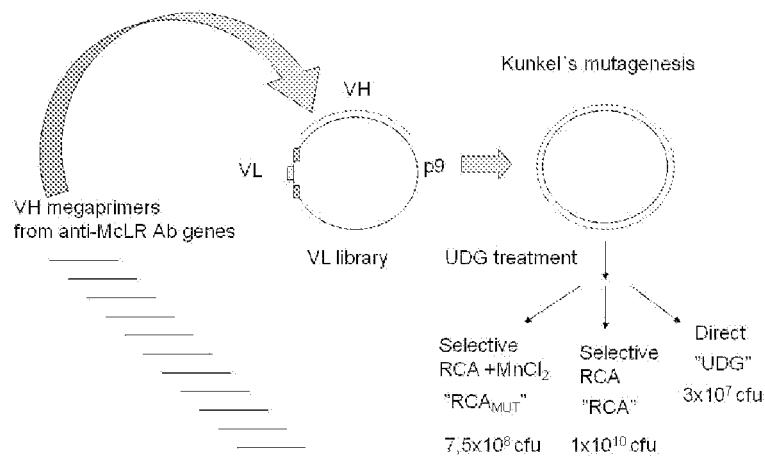
FIG. 5 is a schematic representation of construction of antibody affinity maturation libraries. In this case, the DNA to be incorporated is a PCR product of heavy chain variable domain (VH) gene. This megaprimer is hybridized to ready-made uridylated light chain (VL) randomized ssDNA library, extended with DNA polymerase and ligated to covalently closed circular heteroduplex DNA. Then, the DNA is treated with UDG and the incorporated nascent strand is selectively amplified with RCA.

Mutated RCA amplified DNA may be recircularized by cre recombinase if a 34 bp loxP recombination site, or a modification thereof, is added to the plasmid/phagemid DNA prior to mutagenesis. Cre-loxP technology simplifies recircularization protocol as the recombination step yields same result as DNA digestion, DNA purification and ligation. FIG. 4 shows the number of transformants obtained from 10 ng of an RCA amplified DNA sample by using recombination, digestion/ligation or no treatment.

The efficacy of cre recombinase to circularize the concatemer product produced by RCA was tested with three parallel 10 µl RCA reactions, each containing 10 ng plasmid pIXpAK100r_LoxP1r, 1× Phi29 DNA pol Buffer (MBI Fermentas, Vilna, Lituania), 0.5 mM dNTP's (Finnzymes, Espoo, Finland), 50 µM Exoresistant Random hexamers (MBI Fermentas, Vilna, Lituania) and 5 U Phi 29 DNA polymerase (MBI Fermentas, Vilna, Lituania). The reactions were incubated overnight at 30° C. and heat inactivated at 70° C. for 10 min.

One of the reactions was digested with 10 U HindIII (MBI Fermentas, Vilna, Lituania) in a 50 µl reaction volume for 2 h at 37° C. The reaction was purified with Qiagen PCR purification kit according to the manufacturer's instructions and ligated in a 50 µl reaction with 0.1 U/µl T4 DNA ligase (MBI Fermentas, Vilna, Lituania). The reaction was incubated at 16° C. overnight and heat inactivated at 70° C. for 10 min.

Another 10 µl concatemer sample was set in a 50 µl recombination reaction containing 1× cre recombination buffer (New England Biolabs, Ipswitch, Mass.) and 0.02 U/µl cre recombinase (New England Biolabs, Ipswitch, Mass.). The reaction was incubated at 37° C. for 2 h and heat inactivated at 70° C. for 10 min.

Third 10 µl concatemer sample was not treated. The 50 µl reactions were ethanol precipitated with Pellet Paint Co-precipitant (Novagen) according to the manufacturer's instructions and resuspended in 10 µl Tris-HCl, pH 8.5. The reactions were treated with DpnI to digest unamplified template DNA. 10 µl reactions containing 2 U DpnI (MBI Fermentas, Vilna, Lituania) were incubated for 2 h at 37° C. and heat inactivated at 80° C. for 20 min. 1 µl samples were electroporated to competent SS320 E. coli cells. After 1 h recovery at 37° C., a 100 µl sample was diluted and plated on LA (25 µg/ml chloramphenicol, 10 µg/ml tetracycline, 0.5% glucose). The plates were incubated overnight at 37° C. and colonies counted. The results are shown in FIG. 4. The recombination is a simpler protocol than digestion and ligation but it still yielded the same amount of colonies ($1 \times 10^8$ cfu) from a 10 ng sample, which is 68-fold more than without treatment.

Example 4

Mutagenesis of ds(U)DNA Template

The efficiency of the present method on double-stranded templates was demonstrated with a ds(U)DNA template derived from a pAKBLA3-scFv phagemid.

The ds(U)DNA was first alkali denatured with 200 mM NaOH and then primer extension reactions were carried out as with ssDNA samples. Either EB120 primer or a PCR product of the pAKBLA3-scFv$_{NONSTOP}$ encompassing the scFv gene were used for primer extension and subsequently the UDG treatment and RCA were performed as in Example 1. The effect of the UDG treatment and the selective RCA are listed in Table 3. A 10-fold difference was seen in the frequency of mutated clones between the Kunkel heteroduplex sample and the selectively amplified sample after UDG treatment in both oligo and PCR product primed reactions. Albeit final mutagenesis frequencies 10.3±3.0% and 9.2±2.1% respectively, were relatively modest, the mutagenesis efficiency was markedly increased.

TABLE 3

The effect of selective RCA on primer extension mutagenesis with dsDNA

| | Treatment | | | |
| --- | --- | --- | --- | --- |
| | A. Extended & ligated −UDG | B. Extended & ligated +UDG | C. RCA of A −UDG | D. RCA of B +UDG |
| Random hexamers | none | none | exoresistant | Exoresistant |
| | | oligo | | |
| Functional mutagenesis efficiency (%)$^a$ | 1.0 ± 0.1 | 0.6 ± 0.4 | 0.1 ± 0.02 | 10.3 ± 3.0 |
| Transformants per 10 ng DNA sample (cfu) | $1.2 \pm 0.1 \times 10^4$ | $4.9 \pm 0.6 \times 10^5$ | $4.7 \pm 0.5 \times 10^8$ | $8.6 \pm 1.1 \times 10^6$ |
| | | PCR product | | |
| Functional mutagenesis efficiency (%)$^a$ | 0.9 ± 0.8 | 0.8 ± 0.5 | 0.7 ± 0.1 | 9.2 ± 2.1 |

TABLE 3-continued

| The effect of selective RCA on primer extension mutagenesis with dsDNA | | | | |
|---|---|---|---|---|
| | Treatment | | | |
| | A. Extended & ligated −UDG | B. Extended & ligated +UDG | C. RCA of A −UDG | D. RCA of B +UDG |
| Transformants per 10 ng DNA sample (cfu) | 3.1 ± 0.8 × $10^3$ | 1.6 ± 0.3 × $10^3$ | 4.1 ± 0.1 × $10^7$ | 2.0 ± 0.2 × $10^6$ |

[a]Maximum theoretical functional mutagenesis efficiency is 78%.

Example 5

VH Domain Mutagenesis with PCR Product and Construction of Large Antibody Libraries An antibody library for affinity maturation of microcystin-LR (McLR) binding antibodies was constructed by incorporating 14 anti-McLR IgG heavy chain variable domain (VH-domain) genes into a pool of template DNA consisting of 5×$10^8$ light chain variants. The present method was compared to the Kunkel's mutagenesis. In addition to the regular RCA, amplification was also performed in the presence of 1.5 mM $MnCl_2$ to generate random mutations. Scheme of the affinity maturation library construction is shown in FIG. 5.

Materials and Methods

The 14 VH genes, used as megaprimers in the Kunkel's reaction, were first amplified from the source plasmids by PCR in 50 µl reactions containing 250 µM dNTP's, 50 ng template DNA, 0.2 µM primers EB106 and EB105 and 2.5 U Pfu DNA polymerase (Fermentas, Vilna, Lithuania) in 1×Pfu buffer with $MgSO_4$. The polymerase was added last after the initial denaturation at 95° C. for 2 min. The PCR reaction was cycled 25× with the following steps: den. at 95° C. for 20 s, ann. at 61° C. for 20 s and ext. at 72° C. for 15 s. Final extension was at 72° C. for 3 min. The products were purified with PCR purification kit (Qiagen, Hamburg, Germany) and an asymmetric PCR was set up using the pooled PCR products as template. Same conditions were applied in the asymmetric PCR reaction, except that only EB106 primer was included and cycles augmented to 30. The reaction was purified with PCR purification kit (Qiagen, Hamburg, Germany). The right size and asymmetric PCR reaction of the VH genes were verified by agarose gel analysis.

1251 ng of the VH-megaprimers were phosphorylated in 100 µl T4 PNK buffer A with 20 U T4 PNK (Fermentas, Vilna, Lithuania) with 1 mM ATP and 10 mM DTT. The reaction was incubated at 37° C. for 30 min and affinity purified with Qiagen PCR purification kit. The phosphorylated megaprimer was annealed to 5 µg uridylated single stranded light chain randomized library DNA in the presence of 40 mM Tris-HCl (pH 7.8), 10 mM $MgCl_2$, 10 mM DTT and 0.5 mM ATP in a total 35.5 µl reaction volume. The annealing was performed in a thermal cycler by the following program: 1) at 98° C. for 2 min, 2) at 90° C. for 2 min, 3) at 70° C. for 2 min, 4) at 50° C. for 5 min, 5) at 20° C. for 5 min, 6) at 4° C. for 5 min and subsequently set on ice for 10 min.

The annealed VH-megaprimers were extended and ligated in 200 µl Kunkel's mutagenesis reaction containing 8 µl 25 mM $MgCl_2$, 20 µl 10 mM ATP, 20 µl 100 mM DTT, 20 µl 10 mM dNTP's, 18 U T7 DNA polymerase (NEB, Ipswich, UK) and 15 Weiss Units T4 DNA ligase (Fermentas, Vilna, Lithuania). The components were mixed, incubated 10 min on ice and shifted to RT for 3 h. The Kunkel's reaction was heat inactivated at 70° C. for 20 min.

The mutagenesis reaction was treated with 10 U UDG (NEB, Ipswich, UK) at 37° C. for 1 h and purified with PCR purification kit (Qiagen, Hamburg, Germany) to 50 µl 10 mM Tris-HCl, pH 8.5. 10 µl of the UDG-treated Kunkel reaction was purified with Qiagen kit, 2 µl (240 ng i.e. 4×$10^{10}$ molecules) were taken for RCA and 0.5 µl (60 ng i.e. 1×$10^{10}$) for error-prone RCA ($RCA_{MUT}$). In addition to the UDG-treated DNA, the RCA reaction contained 1 mM dNTP's, 50 µM random primers (Fermentas, Vilna, Lithuania), 4 mM DTT, 0.25 U Inorganic PPase (Fermentas, Vilna, Lithuania) and 100 U Phi29 DNA polymerase (Fermentas, Vilna, Lithuania) in 200 µl phi29 DNA polymerase reaction buffer. The error-prone RCA ($RCA_{MUT}$) was performed similarly in the presence of 1.5 mM $MnCl_2$. The reactions were incubated overnight at 30° C. and heat inactivated at 70° C. for 10 min.

The DNA concatemers produced in RCA and $RCA_{MUT}$ were digested with 200 U HindIII in 1 ml reaction volume overnight at 37° C. The reactions were purified with miniprep kit columns (Qiagen, Hamburg, Germany) in the following way. The 1 ml digest was mixed with 5 ml binding buffer, applied in a 10 ml TERUMO-syringe, which was fastened tightly in a miniprep column. 3 ml of the digest per column was pressed through and, after loading, the purification was continued according to manufacturer's instructions. Total elution volume was 100 µl in 10 mM Tris-HCl pH 8.5. Self-ligation was carried out at 5 ng DNA/µl with 0.05 U/µl T4 DNA Ligase (Fermentas, Vilna, Lithuania) overnight at 16° C. Concentration and purification of the ligation was carried out to 50 µl volume as described above. Samples of the UDG-treated and selectively amplified RCA libraries were transformed to XL-1 cells. DNA was extracted from single colonies and ten samples per library were sequenced (Sequencing Service, Center of Biotechnology, Turku, Finland).

240 ng of the affinity purified UDG-treated DNA (six transformations, 40 ng DNA and 70 µl cells/cuvette) and 6 µg of the re-circularized RCA and $RCA_{MUT}$ DNA (25 transformations, 240 ng and 70 µl cells/cuvette) were transformed to fresh SS320 electrocompetent *E. coli* cells with Bio-Rad Genepulser (Bio-Rad, Hercules, USA) with settings 200Ω, 1.25 kV, 25 µF. After recovery in 24 (UDG-treated) and 100 ml SOC(RCA and $RCA_{MUT}$) at 37° C. 100 rpm for 1 h, samples were diluted and plated on LA (25 µg/ml chloramphenicol, 10 µg/ml tetracycline and 0.5% glucose) for counting transformation efficiency. The rest were plated on 24 cm×24 cm Bioassay dishes (Nunc, Roskilde, Denmark) 20 ml cells/plate. Small plates were incubated at 37° C. and big plates at 30° C. overnight.

The colonies were counted the following day from the dilution plates and 15 ml SB was applied to the big plates and they were scraped with the L-spreader to falcon tubes set on ice. The OD600 nm of the library cell stocks were measured, glycerol was added to final 16% concentration and the cells were stored at −70° C. for use.

Results

Transformation of 240 ng UDG-treated Kunkel reaction directly to SS320 cells resulted in a library of $3 \times 10^7$ members. Selective amplification of the same amount of UDG-treated Kunkel with RCA yielded 12 µg of affinity purified re-circularized DNA. $1 \times 10^{10}$ cfu were gained by transforming half of the 12 µg which is over 300-fold more than without selective RCA. $MnCl_2$, used for simultaneous incorporation of random mutations in RCA, reduced the total amount of affinity purified DNA to 6 µg. Transformation of all gave rise to $8 \times 10^8$ cfu. A lower amount of UDG-treated Kunkel (60 ng) was used to fuel the $RCA_{MUT}$ experiment, because the higher the copy number per template molecule the higher the mutation frequency. Taking the lower input amount into account, 100-fold more colonies were gained by amplifying the DNA in the error-prone conditions, despite the hampering effect of $MnCl_2$ on the catalysis.

Sequencing ten single clones of the UDG-treated Kunkel and selective RCA reaction show that the distribution of different incorporated VH gene variants is more or less similar. Six different variants were found in both sample groups (Table 4). Only 9/10 UDG-treated Kunkel clone sequences were readable from which 1/9 was a nonmutated template clone. In contrast, no template clones were observed among the RCA sample group. The identified VH gene pools are partially overlapping and covering 8/14 incorporated VH genes.

Figure 6:
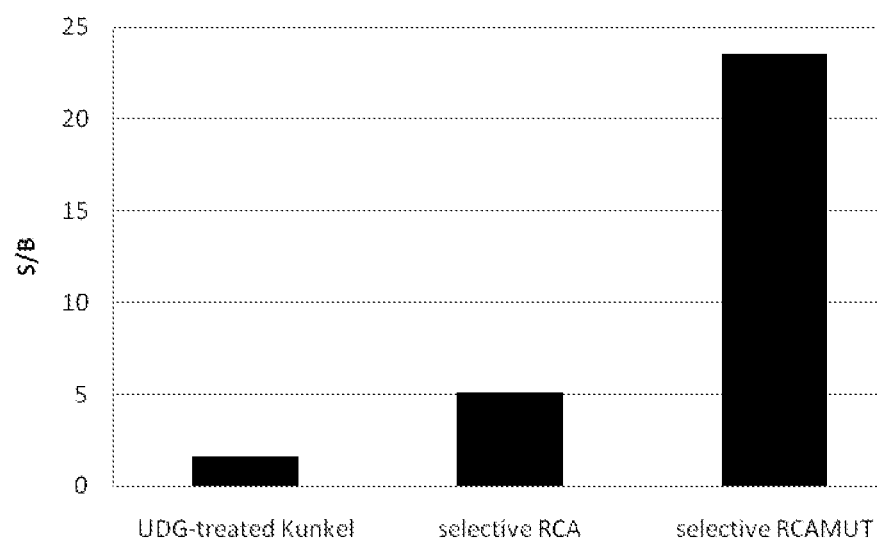
FIG. 6 is a graph illustrating antibody libraries displayed on filamentous phage and enriched by panning two rounds against microcystin-LR (McLR). The enrichment of McLR binding phage was analysed by phage immunoassay using europium chelate labeled anti-phage IgG as label. The results show that the enrichment of McLR binding clones was more efficient in the RCA and $RCA_{MUT}$ libraries compared to the original UDG-treated Kunkel library.
Figure 7:
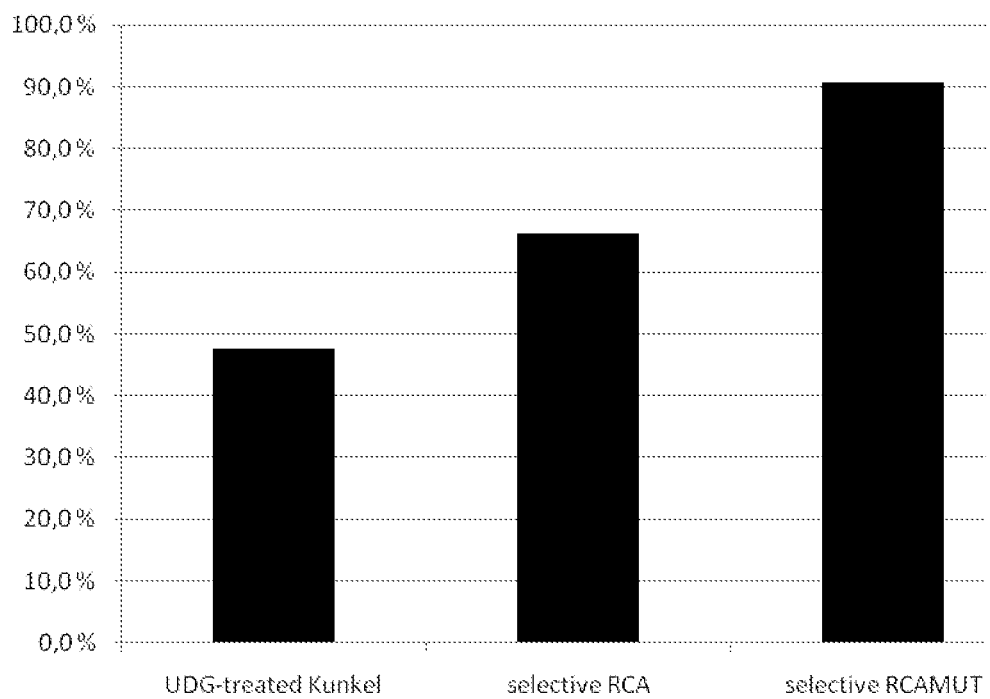
FIG. 7 shows off-rate analysis of the anti-McLR scFv displaying phage libraries. The higher portion (% of input) of remaining phage after free antigen elution indicates higher median affinity of the population. The enriched 2nd round phage stocks were first captured on solid phase bound McLR. The unbound phage were washed away and the bound phage were eluted for 90 min with 1 µM McLR. The remaining phage particles were detected with europium chelate labeled anti-phage antibody. Slower off-rate of the RCA and $RCA_{MUT}$ phage stocks indicates that there are higher affinity antibodies present in the RCA and $RCA_{MUT}$ libraries than in the original UDG-treated Kunkel library.

Anti-McLR scFv antibodies were enriched from the libraries with standard protocols by phage display and biopanning. Phage immunoassay of the enriched phage stocks from the second round shows that the enrichment of McLR binding clones was more efficient in the RCA and $RCA_{MUT}$ libraries compared to the original UDG-treated Kunkel library (FIG. 6). Also the slower off-rate of the RCA and $RCA_{MUT}$ derived 2nd round phage stocks indicates that there are higher affinity antibodies present in the RCA and $RCA_{MUT}$ libraries than in the original UDG-treated Kunkel library (FIG. 7).

Taken together, this Example demonstrates that i) PCR products can be used as mutagenesis primers in the present method, ii) large antibody libraries can be produced from very small amounts of starting DNA by the present method, and iii) the present method may be combined successfully with the error-prone RCA.

| VH gene ID | Kunkel + UDG | Kunkel + UDG + RCA |
|---|---|---|
| Variant A | 1 | 2 |
| Variant B | 2 | 1 |
| Variant C | 2 | 2 |
| Variant D | 1 | 0 |
| Variant E | 1 | 0 |
| Variant F | 1 | 2 |
| Variant G | 0 | 2 |
| Variant H | 0 | 1 |
| Template (nonmutated) | 1 | 0 |
| Total | 9 | 10 |

Example 6

Selective RCA Mutagenesis with Nicking Endonucleases

Selective amplification of the mutated DNA strand in a DNA heteroduplex can also be achieved without uridylated template DNA. At present, there are at least 13 commercially available nicking endonucleases recognizing a variety of sequence elements. Nicking endonucleases cleave only one strand of DNA on a double-stranded DNA molecule. The presence of nicking endonuclease recognition site(s) can be exploited to create nicks in the template strand. Rolling circle amplification on a substrate consisting of a nicked template strand and intact nascently synthesized strand, containing the desired mutations, leads to the superior amplification of the intact mutated strand. The end products can be either directly transformed to cells or re-circularized to monomer units for higher transformation efficiencies. The end product consists almost exclusively of the mutated DNA.

The template DNA can be prepared with any common laboratory strain of E. coli. The template DNA is converted to ssDNA form either directly with filamentous phage or by destroying the other strand of a dsDNA template with a suitable nicking endonuclease treatment followed by an exonuclease treatment. The only requirement for a successful experiment is to find a nicking endonuclease site in the DNA sequence that the cleavage with the nicking endonuclease creates one or several strand breaks in the template strand. It is worth mentioning that depending on the available nicking endonucleases there is also an option to cleave either strand of the same dsDNA recognition sequence (Nt.BbvCI vs. Nb.BbvCI).

Figure 8:
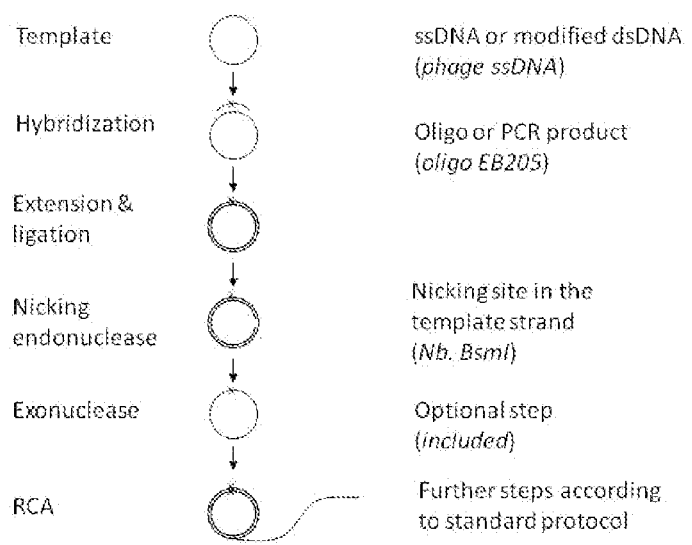
FIG. 8 is a schematic overview of nicking endonuclease mediated selectivity in RCA. Details of Example 6 are shown in parenthesis.

In this experiment a highly variable oligonucleotide, called EB205, was incorporated into a ssDNA template and the mutated clones were selectively amplified by the nicked-template method. Schematic overview is shown in FIG. 8. The template consisted actually of a pool of genes having premade diversity in the CDR-L1, -L3, -H1 and -H2 loops, which was complemented by the CDR-H3 diversification conveyed by the EB205 incorporation.

Materials and Methods

The ssDNA template pHB32x-scFv[NheI] was prepared as described in experiment 1, except that E. coli strain XL-1 Blue (Stratagene, USA) was used as the host for the filamentous phage infection and no uracil was supplemented in the medium. Phosphorylation, annealing and extension of the primer EB205 (purchased from University of Kuopio, Department of Pharmaceutical Chemistry, Finland) was performed as described in Example 1 for 1 µg of template DNA. Also a control Kunkel reaction was carried out without the primer.

The heteroduplex was directly nicked after Kunkel's reaction with 10 U Nb. BsmI (NEB, Ipswich, UK) in 50 µl volume at 65° C. for 1 h. The reaction was heat inactivated at 80° C. for 20 min and purified with PCR purification kit (Qiagen, Hamburg, Germany). The nicked strand was destroyed further with exonuclease III treatment by adding 200 U Exonuclease 111 (Fermentas, Vilna, Lithuania) and reaction buffer provided by the manufacturer. The reaction was incubated at 30° C. for 30 min, inactivated at 70° C. for 20 min and purified with PCR purification kit (Qiagen, Hamburg, Germany). The selective RCA was performed as in Example 1. The DNA concatemer was reduced to plasmid-sized units by diluting the 20 µl reaction to 50 µl supplemented with 1 U Cre recombinase (NEB, Ipswich, UK) and the reaction buffer provided by the manufacturer. The recombination was incubated at 37° C. for 2 h and purified with PCR purification kit (Qiagen, Hamburg, Germany).

1 µl sample of the Kunkel and selective RCA reactions were transformed to XL-1 Blue cells (Stratagene, USA). After 1 h recovery a sample of the transformants were diluted, plated on LA (25 µg/ml chloramphenicol, 10 µg/ml tetracycline, 0.5% glucose) and grown at 37° C. overnight. The rest of the cells were grown overnight in a 5 ml liquid culture 5 ml SB (25 µg/ml chloramphenicol, 10 µg/ml tetracycline, 1% glucose) and miniprep DNA was prepared (miniprep kit, Qiagen, Hamburg, Germany).

400 ng of the library miniprep DNA was double digested with 10 U HindIII and 10 U NheI in 20 µl volume at 37° C. overnight and heat inactivated at 70° C. for 20 min. 5 µl samples were run on 1% agarose gel for analysis. Colony PCR was done with Phire DNA polymerase (Finnzymes, Espoo, Finland) according to manufacturer's instructions using primers EB106 and pAKrev and the following cycling program: (1) Initial den. at 98° C. for 60 s, (2) den. at 98° C. for 5 s, (3) ann. at 66° C. for 5 s, (4) ext. at 72° C. for 20 s and final ext. at 72° C. for 60 s. Steps 2-4 were repeated for 30 cycles. 1/20 of the PCR products were digested with 1 U NheI at 37° C. for 2 h, heat inactivated at 80° C. for 10 min and run on 1% agarose gel for analysis.

Results

Figure 9:
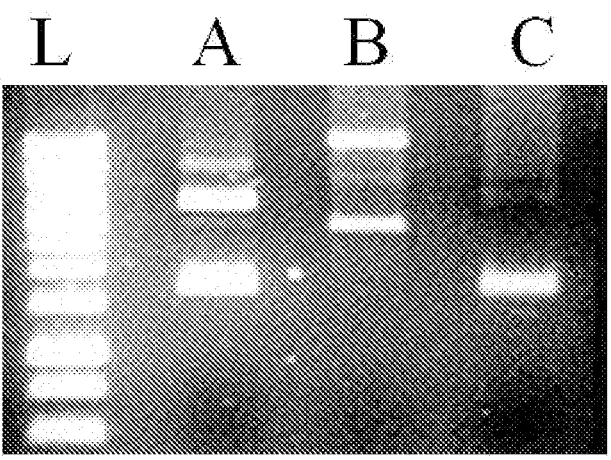
FIG. 9 shows an agarose gel analysis of a Kunkel reaction. Lane L) represents 1 kb Fermentas ladder: lane A) represents template ssDNA; lane B) represents a Kunkel reaction with a primer; and lane C) represents a Kunkel reaction without a primer.

The final stage, CDR-H3 randomization, of a scFv antibody library was performed with nicked-template based selective RCA. First, the randomization oligo was hybridized through its 5' and 3' regions to the complementary VH-gene regions on a single stranded template DNA. Then, the oligo was enzymatically extended and ligated to covalently closed circular DNA. A sample of the Kunkel's mutagenesis was analysed on agarose gel. In a Kunkel reaction supplemented with EB205 the single stranded template band had disappeared and corresponding dsDNA bands appeared. In a control reaction without the primer, the ssDNA remained unaltered (FIG. 9).

Figure 10:
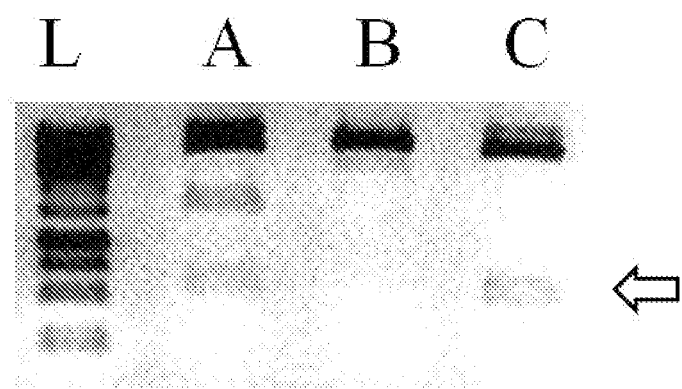
FIG. 10 shows an agarose gel analysis of library DNA HindIII and NheI digestion. HindIII is present in all clones, but NheI only in the template clones. If both sites are present a fragment is released indicated by the arrow. Lane L) represents 1 kb Fermentas ladder; lane A) represents a Kunkel sample; lane B) represents a selective RCA sample; and lane C) represents a template (all molecules cleaved by NheI).

A portion of the Kunkel reaction was treated with the nicking endonuclease Nb. BsmI and amplified in a multiply primed RCA reaction. The resulting DNA concatemer was reduced to circular monomers with cre recombinase, potentiated by the loxP recognition element present in the template, and transformed to cells in parallel with the Kunkel reaction. Digestion of a DNA prep consisting of the transformed library members demonstrated that in the Kunkel sample also template clones remained in the final population whereas no template material was observed in the selective RCA sample (FIG. 10).

To quantitate the difference more closely, a region spanning the CDR-H3 site of scFv gene was amplified by colony PCR. A unique NheI site present in the template sequence was altered by successful mutagenesis. Therefore, NheI digestion of the amplicon was used to analyse the mutagenesis frequency. Among the 17 Kunkel sample clones that gave a product in the colony PCR, 4/17 were resistant to NheI digestion equivalent to 26% mutagenesis efficiency. Respectively, among the 14 selective RCA samples all, 14/14, were resistant to NheI equivalent to 100% efficiency. Thus, according to the results the efficiency is improved to similar extent by selective RCA on the nicked and the UDG-treated template method.

Example 7

Generation of Random Mutations During RCA

Randomly primed RCA with small amount of template causes random mutations at practical frequency for protein engineering purposes. Depending on the application it is sometimes useful to generate both site-directed and random mutations. Selective RCA combined to amplification of picogram amount of template DNA combines these two features. To verify the results, an experiment was performed, in which 25 pg pAK400 ampRloxP plasmid was amplified overnight with multiply primed RCA. The plasmid contains TEM-1 β-lactamase gene. Certain mutations in this gene convert the β-lactamase resistant to ceftazidime. Therefore, to study random mutagenesis in more detail the amplified DNA was transformed to E. coli cells and the clones were plated on agar containing ceftazidime (only mutants grow) and ampicillin (all grow). In addition, the minimal inhibitory concentration (MIC) of the clones was determined to demonstrate the diversity of different mutations.

pAK400 ampRloxP was heat denatured at 95° C. for 3 min. 25 pg plasmid was amplified in 1× phi29 DNA polymerase buffer with 1.5 mM $MnCl_2$, 1 mM dNTP's, 50 µM random hexamers or exo-resistant random primers (Fermentas, St. Leon-Rot, Germany), 0.05 U Inorganic Pyrophosphatase (Fermentas, St. Leon-Rot, Germany) and 10 U phi29 DNA polymerase in 20 µl reaction volume at 30° C. o/n. The RCA reaction was heat inactivated at 70° C. for 10 min and 10 µl of the reaction was recombined and concentrated as earlier. Samples were transformed to XL-1 Blue cells (Stratagene, USA) for plating on LB agar containing 200 µg/ml ampicillin (amp) or 1 µg/ml ceftazidime (ctz) and colonies counted after o/n incubation at 37° C.

The MIC values of the TEM-1 variants were determined by plating. Colonies were picked and grown on a 96-well microtiter plate in 200 µl LB (1 µg/ml ctz and 1% glucose) at 37° C. overnight. The cultures were transferred with a 96-pin replicator on a series of 15 cm Ø LA plates with rising concentration of ctz: 0.6 µg/ml; 1.2 µg/ml; 2.4 µg/ml; 4.8 µg/ml; 9.6 µg/ml; 19.2 µg/ml; 38.4 µg/ml and 38.4 µg/ml. The plates were incubated at 37° C. overnight and the bacterial growth was analysed.

Results

Figure 11:
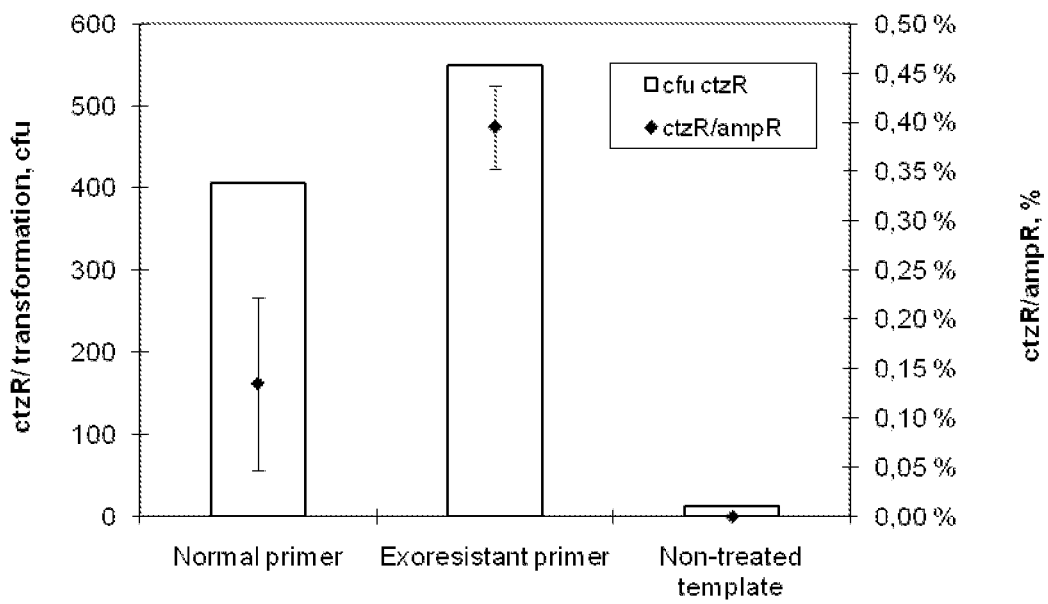
FIG. 11 illustrates generation of ceftazidime resistant TEM-1 β-lactamase variants with multiply primed RCA.

Ceftazidime-resistant β-lactamase variants were generated in the experiment with randomly primed RCA. Random priming with normal hexamers created 407 ctz-resistant (ctzR) colonies per RCA and priming with exo-resistant primers 550, respectively. The ratio of ctzR/ampR colonies, indicating the mutagenesis frequency, was 0.13%±0.09% in the former and 0.40%±0.04% in the latter. Thus, exo-resistant primers induce higher mutagenesis frequency in the same conditions. Interestingly, the total ampR colony counts were higher with normal primers (415667 cfu/RCA) than with exo-resistant primers (145000 cfu/RCA). The natural frequency of ctzR colonies among the template pAK400 ampRloxP ampR transformants was 0.000042%±0.000038%. It is therefore concluded that multiply primed RCA with normal hexamers in the described conditions increases the frequency of random mutations 3000-fold and with exo-resistant primers 9000-fold over the natural occurrence (FIG. 11).

Figure 12:
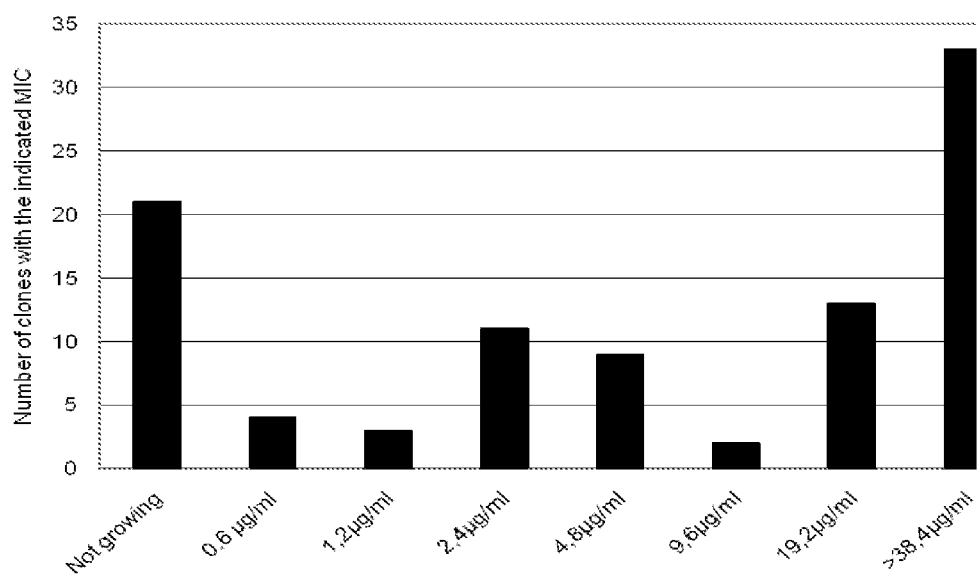
FIG. 12 illustrates resistance characteristics of 93 ctz-resistant clones. The MIC class 0.6 µg/ml includes three negative template controls, which are not resistant to ceftazidime.

These results were further verified by MIC-plating the ctzR colonies. The variable resistance characteristics of 93 samples (and 3 controls of template pAK400 ampRloxP harbouring cells) demonstrate that various mutations and combinations of them were generated in the experiment (FIG. 12). Typically, sequencing revealed 1-3 mutations per TEM-1 β-lactamase gene. The mutations correlated well with the resistance phenotype according to the published literature verifying the relevance of the findings. Also a region of the LacI repressor gene was sequenced of the sample group to calculate the true mutation frequency, because that gene is not under selection in the experiment. One mutation per 836 bp and 669 bp DNA were found based on ten sequenced clones amplified with normal and exoresistant primers, respectively. This mutation frequency corresponds to error-prone PCR performance with mild conditions (typical frequencies: 1-16 mutations per kb).

3. The method according to claim 1, wherein the template is obtained from an ung–/dut– *E. coli* strain.

---

---

The invention claimed is:

1. A method of mutagenizing a nucleic acid molecule, comprising the steps of
   a) providing a uracil containing template comprising a target nucleic acid molecule in a circular DNA vector,
   b) providing at least one mutagenesis primer containing the mutations to be introduced into the target nucleic acid molecule,
   c) annealing the mutagenesis primer to the target nucleic acid molecule,
   d) carrying out a single isothermal primer extension with a DNA polymerase without significant strand displacement activity and ligation reaction to form a double-stranded heteroduplex wherein one strand is a template strand and the other strand is a newly synthesized mutated strand,
   e) rendering the template strand unfavorable for rolling circle amplification (RCA) by a treatment with uracil-DNA glycosylase (UDG),
   f) amplifying the mutated strand by multiple-primed rolling circle amplification, and
   g) transforming the amplified DNA to a suitable host.

2. The method according to claim 1 comprising a further step between steps f) and g), wherein the amplified DNA is converted to plasmid size-units by (i) digestion with a restriction enzyme, (ii) digestion with a restriction enzyme and ligation with a DNA ligase, or (iii) by recombination.

4. The method according to claim 1, wherein the mutagenesis primer contains at least one site-directed mutation.

5. The method according to claim 1, wherein the mutagenesis primer contains at least one random mutation.

6. The method according to claim 1, wherein the rolling circle amplification is performed with phi29 DNA polymerase.

7. The method according to claim 1, wherein the rolling circle amplification is performed in a condition that produces random mutations.

8. The method according to claim 7, wherein said condition is a member selected from the group consisting of decrease in template amount, supplementation of the rolling circle amplification with $MnCl_2$ and supplementation of the rolling circle amplification with nucleotide triphosphate analogs.

9. The method according to claim 1, wherein the nucleic acid molecule to be mutagenized is in the form of double-stranded DNA, and the method comprises opening the double-stranded structure prior to step c).

10. A method of mutagenizing a nucleic acid molecule, comprising the steps of
    a) providing a template comprising a target nucleic acid molecule in a circular DNA vector, wherein the template is methylated and uridylated dsDNA,
    b) providing at least one mutagenesis primer containing the mutations to be introduced into the target nucleic acid molecule, c) annealing the mutagenesis primer to the target nucleic acid molecule, d) carrying out a single isothermal primer extension with a DNA polymerase without significant strand displacement activity and ligation reaction to form a double-stranded heteroduplex wherein one strand is a template strand and the other strand is a newly synthesized mutated strand, e) rendering the template strand unfavorable for rolling circle amplification (RCA) by a treatment with UDG and DpnI restriction enzyme, f) amplifying the mutated strand by multiple-primed rolling circle amplification, and g) transforming the amplified DNA to a suitable host.

11. The method according to claim 10, wherein the template is obtained from a dam+/ung−/dut− *E. coli* strain.

12. The method according to claim 10, wherein the mutagenesis primer contains at least one site-directed mutation.

13. The method according to claim 10, wherein the mutagenesis primer contains at least one random mutation.

14. The method according to claim 10, wherein the rolling circle amplification is performed with phi29 DNA polymerase.

15. The method according to claim 10, wherein the rolling circle amplification is performed in a condition that produces random mutations.

16. The method according to claim 10, wherein the nucleic acid molecule to be mutagenized is in the form of double-stranded DNA, and the method comprises opening the double-stranded structure prior to step c).

* * * * *

SEQUENCE LISTING

<160> NUMBER OF SEQ ID NOS: 2

<210> SEQ ID NO 1
<211> LENGTH: 74
<212> TYPE: DNA
<213> ORGANISM: Artificial
<220> FEATURE:
<223> OTHER INFORMATION: Mutagenesis oligonucleotide
<220> FEATURE:
<221> NAME/KEY: misc_feature
<222> LOCATION: (29)..(49)
<223> OTHER INFORMATION: n is a, c, g, or t

<400> SEQUENCE: 1
ctagtgtacc ctgacccag tccatagcnn nnnnnnnnn nnnnnnnnna cgagcacagt      60
agtagacagc cgtg                                                      74

<210> SEQ ID NO 2
<211> LENGTH: 51
<212> TYPE: DNA
<213> ORGANISM: Artificial
<220> FEATURE:
<223> OTHER INFORMATION: Mutagenesis oligonucleotide
<220> FEATURE:
<221> NAME/KEY: misc_feature
<222> LOCATION: (24)..(26)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t

<400> SEQUENCE: 2
cagcctccgg atttacgttc tccnnntacn nnatgcactg ggtccgtcag g             51